(12) United States Patent 
Rosenberg

(10) Patent No.: US 6,926,523 B2
(45) Date of Patent: Aug. 9, 2005

(54) SPRING CUSHIONED ORTHODONTIC BRACKET

(76) Inventor: Farel Rosenberg, 9305 Beverly Crest Dr., Beverly Hills, CA (US) 90210

(*) Notice: Subject to any disclaimer, the term of this patent is extended or adjusted under 35 U.S.C. 154(b) by 2 days.

(21) Appl. No.: 10/741,331

(22) Filed: Dec. 22, 2003

(65) Prior Publication Data

US 2005/0136369 A1 Jun. 23, 2005

(51) Int. Cl.[7] ............................................. A61C 3/00
(52) U.S. Cl. ........................................................ 433/9
(58) Field of Search ......................... 433/8, 9, 10, 11, 433/13, 21, 22

(56) References Cited

U.S. PATENT DOCUMENTS

| | | | | |
|---|---|---|---|---|
| 4,487,581 A | * | 12/1984 | Adler | 433/16 |
| 4,687,441 A | * | 8/1987 | Klepacki | 433/8 |
| 2002/0119414 A1 | * | 8/2002 | Orikasa | 433/10 |

* cited by examiner

Primary Examiner—Melba Bumgarner
(74) Attorney, Agent, or Firm—Albert O. Cota

(57) ABSTRACT

An orthodontic bracket containing a flexible element incorporated between its base and bracket to permit installation on each tooth where needed is described. With the base firmly anchored on a tooth and a semi rigid archwire ligated to the bracket, flexible compliance between each tooth and its correcting force is obtained assuring comfort during the orthodontic procedure.

6 Claims, 3 Drawing Sheets

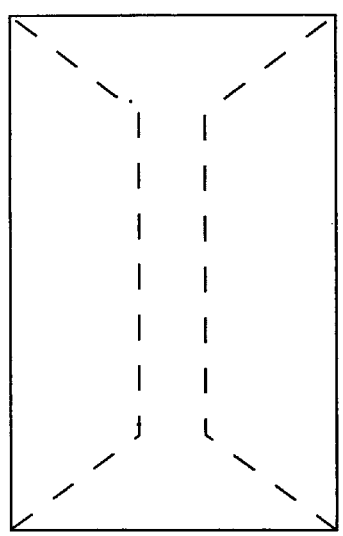
A
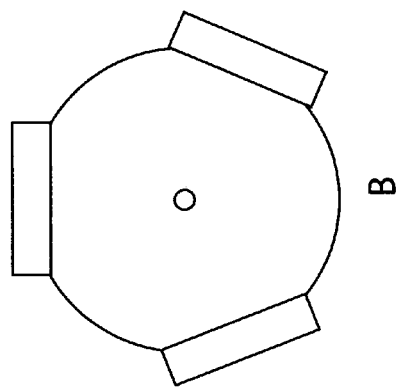
B
FIG. 3

SPRING CUSHIONED ORTHODONTIC BRACKET

Corrective forces in present day orthodontic practice are created by cementing the base of a slotted bracket to each tooth to be moved. Then a semi rigid archwire in the mouth is passed through the slot, to create corrective forces. This involves considerable bending of the archwire; a tie wire is then used to secure the archwire in each slot. After this procedure is carried out, in out, up down, tilt and torque forces are created which move each tooth to a more orthodontically correct position. Repetition of the process over a period finally achieves an overall correction, which is more satisfactory from a cosmetic and functional standpoint. The present process consumes a considerable amount of time and is wasteful of skilled labor to accomplish the result.

The present invention utilizes a flexible element between a cementable base and a slotted bracket head. After the base is cemented to a tooth, the spring element can be used to create cushioned corrective forces. Cushioned forces come about when ligating wires are applied and tightened.

BRIEF DESCRIPTION OF THE DRAWINGS

FIG. 3A is a plan view of the spring element 7 in the rectangular shape with creasing illustrated underneath in dashed lines.

FIG. 3B is a plan view of the spring element 7 in the non-circular shape with multi-sided creasing illustrated with solid lines on three equidistant peripheral areas.

DESCRIPTION OF THE INVENTION

Figure 1:
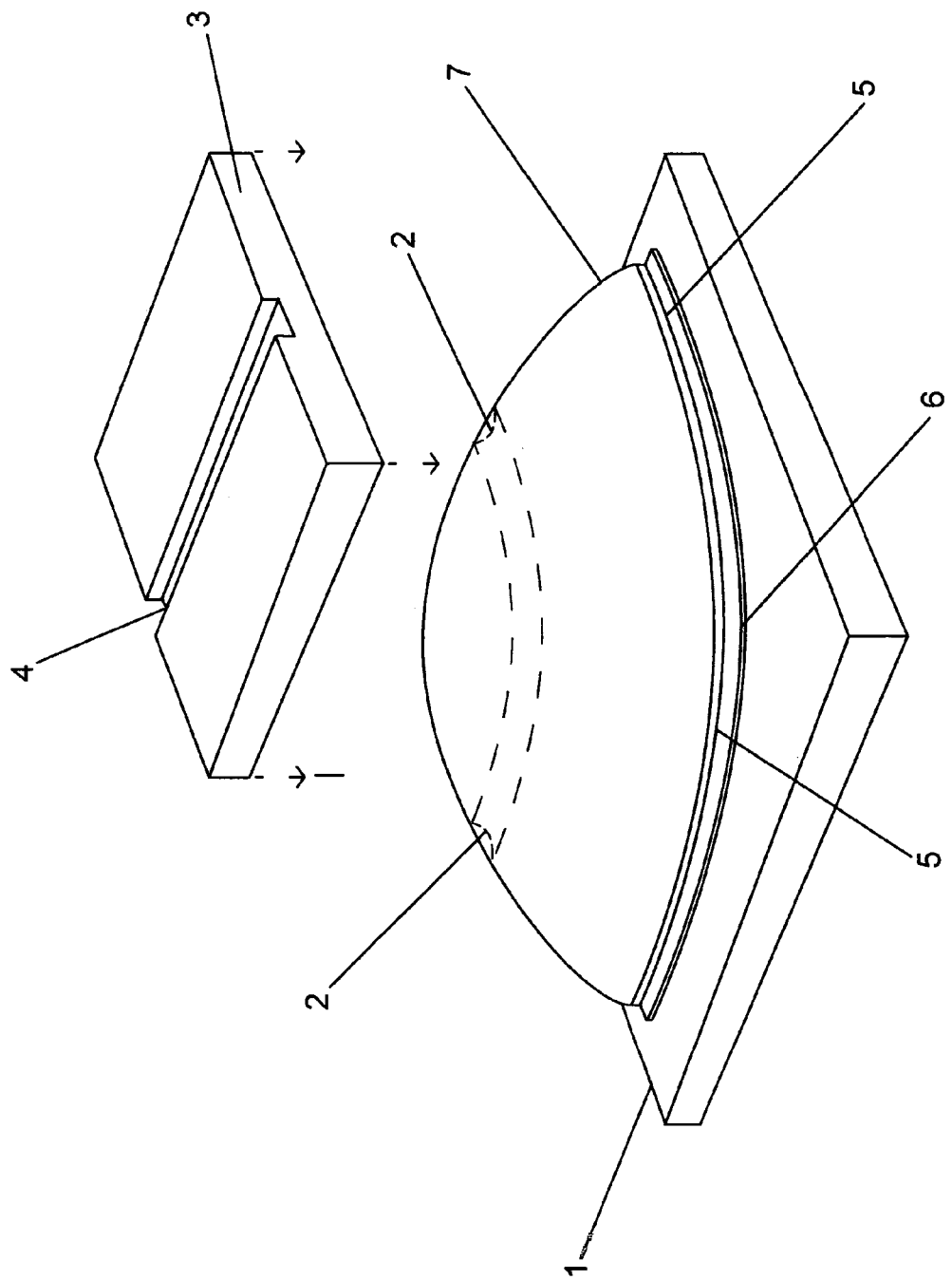
FIG. 1 is a partial isometric view of the invention illustrating the spring element 7 attached to the base piece 1 with the bracket head 3 positioned above the spring element for clarity.
Figure 2:
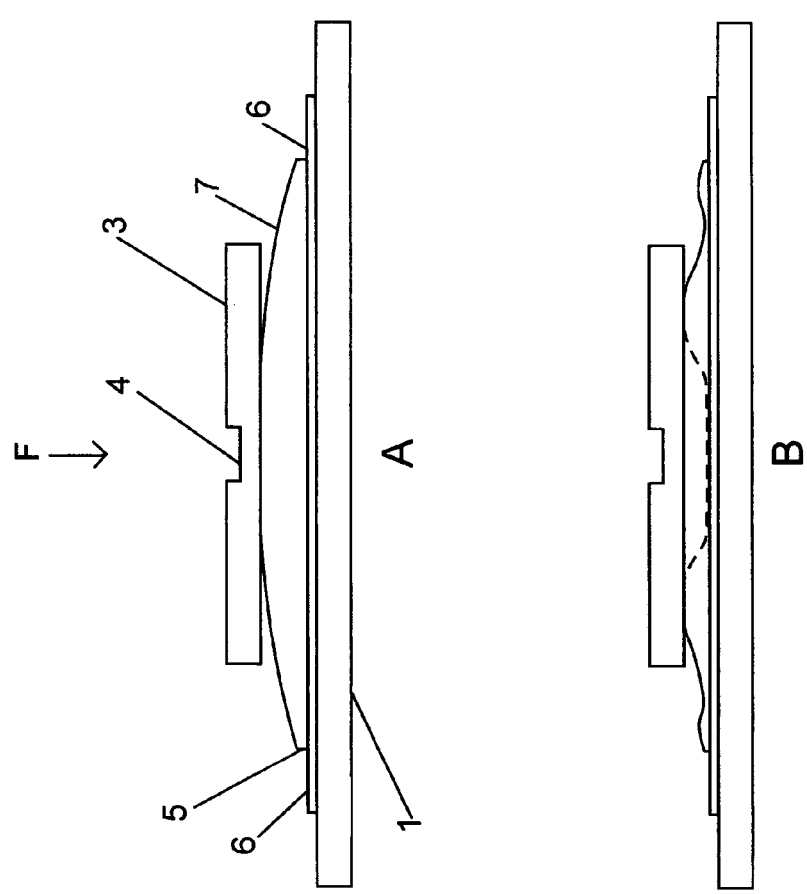
FIG. 2A is a right side view of the invention with the spring element 7 illustrated in its fully extended form.
FIG. 2B is a right side view of the invention with the spring element 7 illustrated in its partially collapsed form.

The general features of the present invention are illustrated in FIGS. 1 to 3. In FIG. 1 a base piece 1 is cemented to a tooth to be moved. The base piece 1 is also welded to flexible element 7 which in turn is joined to bracket head 3 containing archwire slot 4. Spring element 7 can accommodate compression, extension or angular movement between the base piece 1 and bracket head 3. When a relatively rigid archwire is passed through slot 4 and tied down by ligation wires, it can be seen that a number of forces can be created between the bracket head, spring element and base. Depending on the physical design of the spring element, the tooth may be moved to an in-out, up-down, tilting, rotation, or torque movement as required for positional tooth correction without complex wire bending.

The spring element 7 is a thin, dome whose circumferential lip 6 can be joined to base 1. It is also joined to slotted bracket 3. When the base 1 is cemented to a tooth and bracket 3 is attached to an archwire in the mouth, flexure of the spring element 7 occurs between the bracket and the tooth. By variations in the location of the cementable base or by distorting the bracket head, a variety of correction forces can be achieved.

A significant feature of the invention is the means by which spring action is achieved in spring element 7. In the embodiment shown in FIG. 1 the element is dome shaped and is provided with a vertical "skirt" 5 around its periphery as well a peripheral, weldable lip 6. When a vertical force is applied to the top of the dome via bracket head 3, a concavity 2 (FIG. 1) is created. Deformation of the dome is limited by contact with base piece 1 (FIGS. 2A and 2B). Thus, there are two equilibrium positions of the dome: partially collapsed and fully extended with the spring force tending to restore the latter.

FIG. 2 illustrates the two equilibrium positions with FIG. 2A showing the invention in the fully extended position and FIG. 2B depicting the partially collapsed position.

The dome may be formed by the use of an embossing die in relatively thin metal, which also forms the skirt and lip and serves to enable spot welding to base piece 1.

Spring element 7 can also be in square, rectangular, or multi-sided form where the shape can be chosen to accommodate a particular base or bracket head. The two-position spring property can be imparted to a non-circular element by "creasing" the metal as shown in FIG. 3 (A and B) which multiplies the surface of the spring and allows welding of the element. The crease helps bring about directional definition (direction and depth) of the spring movement.

What is claimed is:

1. A flexible, cushioned orthodontic bracket comprised of:
   A. a slotted bracket head;
   B. a spring element mounted to said bracket head, wherein said spring element is in the form of a hollow cone shaped dome terminated at its open end by a skirt and weldable lip around its perimeter; and
   C. a base piece attached to said spring element whereby pressure on the bracket head will cause flexion on the spring element, distortion of said element and transmission of the pressure to the base piece when an assembled bracket is cemented to a tooth and archwire is inserted and ligated in the slot in said bracket head.

2. The flexible, cushioned orthodontic bracket as described in claim 1 in which said spring element provides the desired forces: in-out, up-down, tilt, rotation and torque directions as adjusted buy an orthodontist, who may manually distort specific brackets in a prearranged manner.

3. The flexible, cushioned orthodontic bracket as described in claim 1 in which said spring element cushions the bracket in its reaction with a semi rigid archwire.

4. The flexible, cushioned orthodontic bracket comprised of:
   A. a slotted bracket head;
   B. a spring element mounted to said bracket head, in which said spring element is in the form of a multisided plate, which has been prestamped to form creases, said creases causing deformation in the plate, when subject to pressure and snap back when pressure is removed, and
   C. a base piece attached to said spring element whereby pressure on the bracket head will cause flexion on the spring element, distortion of said element and transmission of the pressure to the base piece when an assembled bracket is cemented to a tooth and archwire is inserted and ligated in the slot in said bracket head.

5. The flexible, cushioned orthodontic bracket as described in claim 4 in which said spring element prestamped creases determine the direction of bending when the element is deformed and the creation of in-out, up-down, tilt and torque forces for orthodontic purposes.

6. The flexible, cushioned orthodontic bracket as described in claim 4 in which said spring element prestamped creases allow the direction, depth and extent of movement to be predefined for correction of the element.

* * * * *